US006533785B1

(12) United States Patent
Frigg et al.

(10) Patent No.: US 6,533,785 B1
(45) Date of Patent: Mar. 18, 2003

(54) CLAMP FOR AN EXTERNAL BONE FIXATION DEVICE

(75) Inventors: Robert Frigg, Bettlach (CH); Markus Hehli, Frauenkirch (CH)

(73) Assignee: Synthes (USA), Paoli, PA (US)

( * ) Notice: Subject to any disclaimer, the term of this patent is extended or adjusted under 35 U.S.C. 154(b) by 264 days.

(21) Appl. No.: 09/705,716

(22) Filed: Nov. 6, 2000

Related U.S. Application Data

(63) Continuation of application No. PCT/CH98/00185, filed on May 7, 1998.

(51) Int. Cl.[7] .................................................. A61B 17/56
(52) U.S. Cl. ........................................................ 606/53
(58) Field of Search .............................. 606/53–59, 60, 606/61

(56) References Cited

U.S. PATENT DOCUMENTS

| | | | | |
|---|---|---|---|---|
| 4,271,832 A | * | 6/1981 | Evans et al. .................. 606/54 |
| 5,053,034 A | * | 10/1991 | Olerud ......................... 606/54 |
| 5,304,177 A | | 4/1994 | Pennig | |
| 5,320,623 A | * | 6/1994 | Pennig ......................... 403/59 |
| 5,571,102 A | * | 11/1996 | Cavagna et al. .............. 606/61 |
| 5,746,741 A | * | 5/1998 | Kraus et al. .................. 606/53 |
| 5,827,283 A | * | 10/1998 | Groiso et al. ................. 606/54 |
| 5,921,985 A | * | 7/1999 | Ross et al. .................... 606/54 |
| 5,976,133 A | * | 11/1999 | Kraus et al. .................. 606/54 |
| 6,001,097 A | * | 12/1999 | Campopiano et al. ....... 606/102 |
| 6,080,153 A | * | 6/2000 | Mata et al. ................... 606/54 |
| 6,342,054 B1 | * | 1/2002 | Mata ............................ 606/54 |

FOREIGN PATENT DOCUMENTS

| | | | |
|---|---|---|---|
| DE | 93 20 834 | 3/1995 | ........... A61B/17/60 |
| EP | 0 593 321 A1 | 4/1994 | ........... A61B/17/60 |
| WO | WO 97/41790 | 11/1997 | ........... A61B/17/60 |

* cited by examiner

*Primary Examiner*—Michael Peffley
*Assistant Examiner*—Peter J Vrettakos
(74) *Attorney, Agent, or Firm*—Pennie & Edmonds LLP

(57) ABSTRACT

A clamp for an external fixation device includes a basic body fitted with a first, continuous borehole for receiving a longitudinal support and a second, continuous borehole disposed perpendicular to the first borehole and partly intersecting it for receiving a tension bolt. The tension bolt includes a transverse borehole for receiving a bone fixation device, such as a bone pin, and further includes threading at one free end for engagement with a nut that forms a stop against the basic body. Tightening of the nut on the tension bolt permits the bone fixation device to be held against the basic body. An additional, threaded borehole is provided in the basic body, terminates in the second borehole, and receives a fixation screw. The diameter of the tension bolt can be less than the diameter of the second borehole and the fixation screw can be used to position the tension bolt so that it lies across a portion of the first borehole and bears tangentially against the longitudinal support.

17 Claims, 2 Drawing Sheets

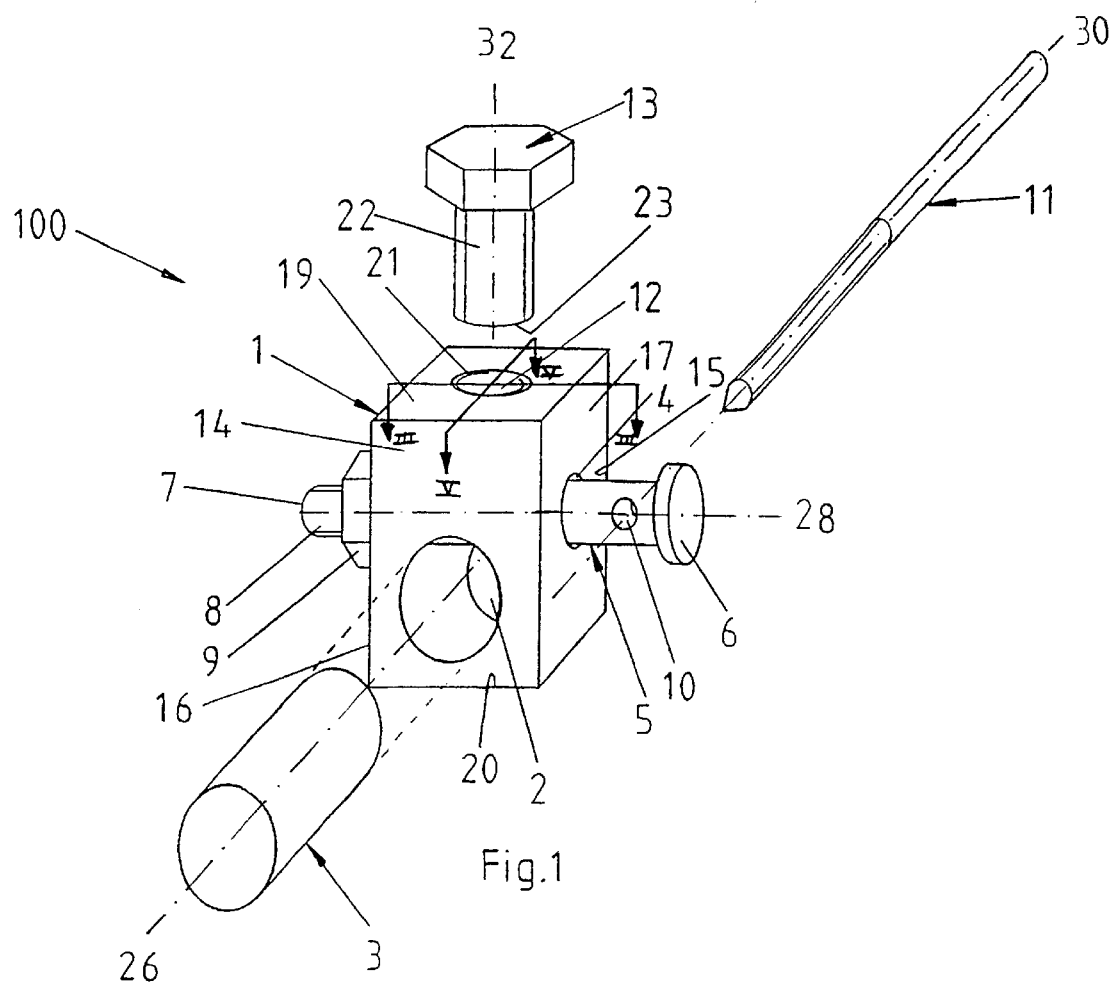
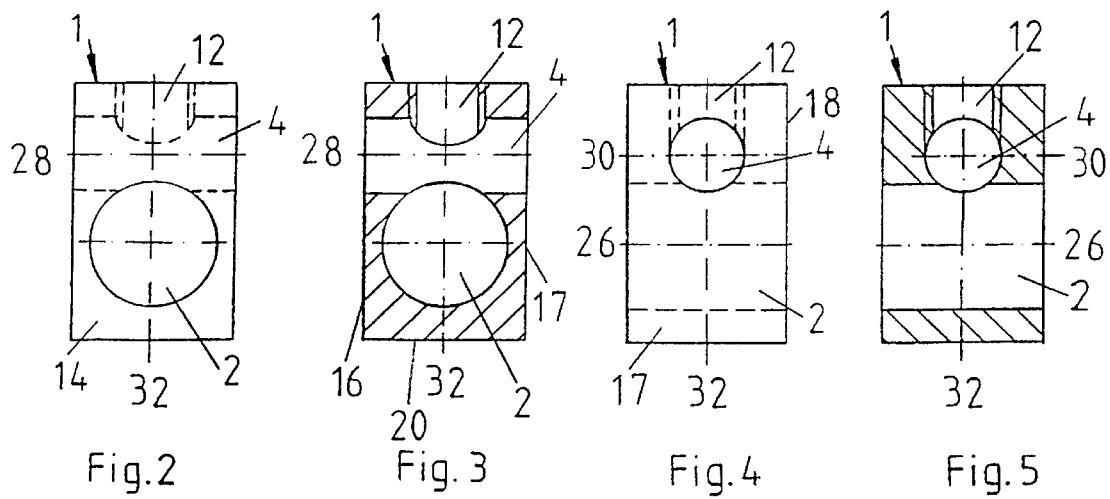

CLAMP FOR AN EXTERNAL BONE FIXATION DEVICE

CROSS-REFERENCE TO RELATED APPLICATIONS

This application is a continuation of the U.S. National Stage designation of co-pending International Patent Application PCT/CH98/00185, filed May 7, 1998, the entire content of which is expressly incorporated herein by reference thereto.

FIELD OF THE INVENTION

The invention relates to a clamp used in an external bone fixation device. More particularly, the invention relates to a clamp for coupling a longitudinal support and a bone fixation device such as a Schanz screw or any other suitable bone fastener.

BACKGROUND OF THE INVENTION

Open fractures of the 2nd and 3rd degrees, infection pseudoarthroses and corrective interventions for axial deviations and length differences are among the most important indications for external fixation devices. A number of clamps for use in such external fixation devices are already known, however prior art clamps have the drawback of requiring exceedingly accurate manufacture and concomitantly high cost.

There exists a need for an improved clamp that has a simple design and can be manufactured with relatively low tolerances, yet still permits the desired component fixation for palliative effect.

There further exists a need for an improved clamp with a design that is free of tight tolerances, and thus can be used with a wide range of external fixation devices. Such a versatile clamp can offer ease of high production runs and simplified logistics, thereby meeting the needs of developing and threshold countries. Despite the simple, manufacturing-friendly design, the clamp should offer many degrees of freedom, similar to conventional, more complex and costly clamps of the prior art.

Additionally, there is a need for an improved clamp designed with features having generous tolerances so that the longitudinal support may be bent to fit the anatomy. Such a design is useful, for example, when tending to pelvic fractures, which currently are typically treated only with pre-bent longitudinal supports or with several longitudinal supports mutually connected by articulating jaws.

The present invention provides a clamp that is capable of providing these improvements.

SUMMARY OF THE INVENTION

The present invention is related to a clamp for an external bone fixation device, and includes a body having first, second and third boreholes extending therein, a longitudinal support, a coupling member for coupling to a bone fastener, and a tightening component. The first borehole extends along a first longitudinal axis and is configured and dimensioned for receiving the longitudinal support, while the second borehole extends along a second longitudinal axis and is configured and dimensioned for receiving the coupling member. The third borehole extends along a third longitudinal axis and is configured and dimensioned for receiving the tightening component. The first longitudinal axis is oriented at an angle with respect to the second longitudinal axis, and the third longitudinal axis is substantially perpendicular to both the first and second longitudinal axes. The third borehole extends from a surface of the block to intersect the second borehole, and the first and second boreholes at least partially intersect each other. In addition, the longitudinal support in the first borehole and the coupling member in the second borehole are simultaneously fixed in position when the tightening component bears against the member and the member bears against the longitudinal support.

In the preferred embodiment, the third borehole is threaded and only extends to the intersection with the second borehole, with the tightening component also being correspondingly threaded to engage the threaded borehole. The coupling member includes a first end and a second end, and a through hole proximate the first end for receiving a bone fastener. Also, the first and second boreholes are substantially perpendicular to each other. The coupling member may further include a threaded portion proximate the second end, and a nut may be provided for threadably engaging the threaded portion of the coupling member. The body may have a rectangular form with six faces, each face having smooth or beveled edges. The body may instead have a parallelepiped shape. The member may be generally cylindrical and have a member diameter, while the second bore may have a second diameter, with the member diameter being smaller than the second diameter to permit the member to freely move within the second bore. Furthermore, the through hole may have a hole diameter, the bone fastener may have a fastener diameter, and the hole diameter may be about the same as the fastener diameter.

In the preferred embodiment, the tightening component is formed of a first material and the body is formed of a second material, with the first material being harder than the second material. The first material may be steel while the second material may be aluminum. In addition, the longitudinal support may be formed of a third material, with the first material being harder that the third material.

The present invention also is related to a clamp for simultaneously fixing the positions of a longitudinal member and a bone fastener with respect to each other. The clamp includes a parallelepiped body with two unthreaded holes and one threaded hole extending therein, a member for coupling to a bone fastener, a nut for coupling to the member, and a threaded tightening component. The threaded tightening component threadably engages the threaded hole, and when the threaded tightening component bears against the member, the member can bear against the longitudinal member.

The invention further relates to a clamp comprising a parallelipipedic basic body and a tension bolt. The basic body is fitted with a first and continuous borehole to receive a longitudinal support, and also is fitted with a second and continuous borehole disposed perpendicular to the first borehole and partly crossing it. The tension bolt may have a head, and can be inserted by its free end into the second borehole, the head forming a stop against the basic body. Proximate its free end, the tension bolt is threaded, the threads provided for engaging a nut that forms a stop against the basic body. The tension bolt may include an unthreaded shank part located between the threaded portion and the head, and in a preferred embodiment also is fitted with a transverse borehole in the unthreaded shank part proximate the head to receive a bone fixation device. The transverse borehole can be moved by the nut into the proximity of the second borehole, with a bone fixation device being displaceable in this process to come to rest against the basic body. The basic body further is fitted with a threaded borehole running perpendicular to both the first and second continuous bore holes, terminating in the second borehole and receiving a fixation screw. In a preferred embodiment, the diameter of the tension bolt is smaller than the diameter of the second borehole, so that the tension bolt can be moved by the fixation screw into the zone of the second borehole to tangentially rest against the longitudinal support.

In one embodiment, the basic body is made of aluminum, and the bone fixation device is preferably made of a material that is harder than that of the basic body. The tension bolt is preferably made of steel, and also is preferably made of a material harder than that of the basic body. In addition, the longitudinal support is preferably made of a softer material than that of the tension bolt.

Advantageously, in a preferred embodiment, the clamp body is only used to receive the two tightening elements (one for the longitudinal support and the other for the bone screw). Furthermore, the position of the tightening element for the bone screw also is fixed when the longitudinal support is fixed. The clamp may permit bone screws of different diameters to be tightened. Also, the clamp design is size-independent—that is, the same clamp design is applicable to fractures of thighs, lower arms and fingers.

BRIEF DESCRIPTION OF THE DRAWINGS

Preferred features of the present invention are disclosed in the accompanying drawings, wherein similar reference characters denote similar elements throughout the several views, and wherein:

FIG. 1 is a partially exploded, perspective view of a clamp of the present invention;

FIG. 2 is a front view of the basic body of the clamp of FIG. 1;

FIG. 3 is a cross-sectional view parallel to the front surface of the basic body taken along line III—III;

FIG. 4 is a side view of the basic body of the clamp of FIG. 1;

FIG. 5 is a cross-sectional view parallel to the side surface of the basic body taken along line V—V;

DETAILED DESCRIPTION OF PREFERRED EMBODIMENTS

Figure 7:
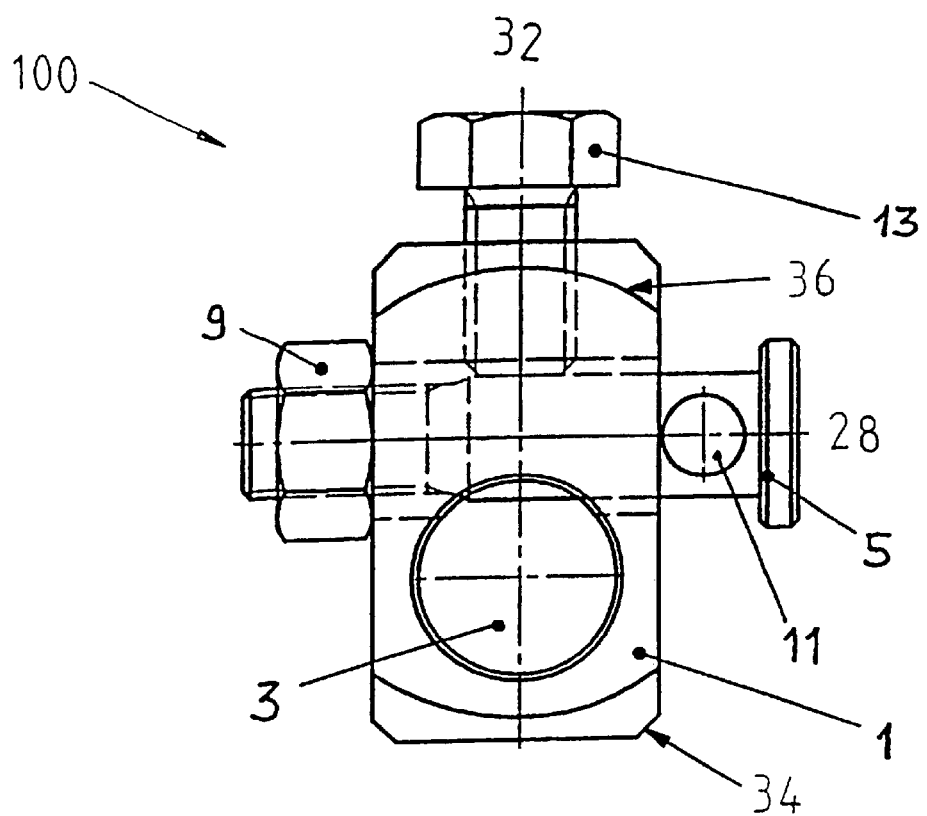
FIG. 7 is a partial cross-sectional view of an assembled clamp of the present invention.

Referring to FIGS. 1–5, a clamp 100 for an external bone fixation device includes basic body 1 having a front face 14, a rear face 15, two side faces 16 and 17, a top face 19 and a bottom face 20. In a preferred embodiment, basic body 1 has a parallelepipedic shape, and is preferably formed of aluminum. However, in alternate embodiments, a non-parallelepipedic shape may be used. For example, as shown in FIG. 7, beveled edges 34 and arcuate surfaces 36 may be included. In addition, although faces 14, 15, 16, 17 have like dimensions (i.e., faces 14 and 15 are symmetric, faces 16 and 17 are symmetric, and faces 14, 15, 16, 17 have similar overall dimensions), and faces 19, 20 have like overall dimensions, the dimensions of the faces instead may be varied.

Basic body 1 includes a first, continuous borehole 2 extending from front face 14 to rear face 15 and disposed about central longitudinal axis 26, and is configured to receive a longitudinal support 3. Longitudinal support 3 may be solid or hollow, and its surface may be smooth or rough. Preferably, longitudinal support 3 is formed of aluminum. Basic body 1 also is fitted with a second, continuous borehole 4 extending from side face 16 to side face 17 and disposed about central longitudinal axis 28. Preferably, second borehole 4 is disposed perpendicular to first borehole 2, and partly intersects borehole 2 as shown for example in FIGS. 2–5.

Figure 6:
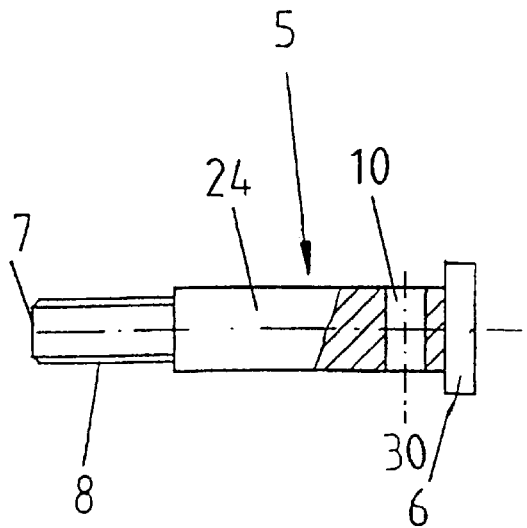
FIG. 6 is a partial longitudinal cross-sectional view of the tension bolt of FIG. 1.

Referring to FIGS. 1, 6 and 7, clamp 100 is provided with a tension bolt 5 having a head 6 and circular shank 24. Tension bolt 5 is provided with a threaded portion 8 in the vicinity of end 7. A transverse borehole 10 extends through circular shank 24 of tension bolt 5 in the vicinity of head 6. The transverse borehole 10 is disposed about central longitudinal axis 30, and is configured to receive a bone fixation device 11, such as a Schanz screw or any other suitable bone fastener. Tension bolt 5 is inserted into second borehole 4. When inserted first through face 17, for example, tension bolt 5 is permitted to protrude beyond opposite face 16 so that threaded portion 8 is exposed. Head 6 has a diameter that is larger than the diameter of second borehole 4, thus forming a stop at side face 17 of basic body 1 and limiting the travel of tension bolt 5. Tension bolt 5 preferably is secured to basic body 1 using a nut 9 which is threadably received on threaded portion 8 near free end 7 of tension bolt 5, thus forming a second stop at opposite side face 16 of basic body 1. Preferably, tension bolt 5 is formed of steel.

When a bone fixation device 11 is inserted into transverse borehole 10 of a tension bolt 5, the angulation of bone fixation device 11 may be set. In particular, when tension bolt 5 is disposed in borehole 4, tension bolt 5 (carrying bone fixation device 11) may be freely rotated within borehole 4 through a full 360°. In addition, the axial position of bone fixation device 11 also may be adjusted with respect to borehole 4 by freely moving tension bolt 5 within borehole 4. The position of bone fixation device 11 may be fixed by engaging nut 9 with threaded portion 8, and thus causing tension bolt 5 to travel within second borehole 4.

Travel of tension bolt 5 is arrested when bone fixation device 11, and consequently transverse borehole 10, have been displaced to the vicinity of second borehole 4, such that bone fixation device 11 comes to rest against side face 17 of basic body 1, as shown for example in FIG. 7. Advantageously, when using a bone fixation device 11 formed of a harder material than that of basic body 1, for example forming bone fixation device 11 from steel and forming basic body 1 of aluminum, clamping may be facilitated as a result of the material hardness differences.

In a preferred embodiment, basic body 1 additionally includes a borehole 12 with internal threading 21 and disposed about central longitudinal axis 32, which preferably is perpendicular to both the first and second boreholes 2, 4 and their respective central longitudinal axes 26, 28. Preferably, threaded borehole 12 extends from top face 19 and terminates in borehole 4, and is configured to hold a fixation screw 13 having a like-externally-threaded shank 22. When a fixation screw 13 is located in borehole 12, it may extend therethrough to contact and fix tension bolt 5, inserted into second borehole 4, as desired. In particular, free end 23 of fixation screw 13 may bear against circular shank 24 of tension bolt 5. The diameter of shank 24 of tension bolt 5 may be smaller than the diameter of second borehole 4, and thus fixation screw 13 may be used to force tension bolt 5 to protrude partially into the first borehole 2, which receives longitudinal support 3. Consequently, when a longitudinal support 3 is disposed in borehole 2, a tension bolt 5 may bear against longitudinal support 3 due to fixation screw 13 bearing against tension bolt 5. With longitudinal support 3 disposed in borehole 2, basic body 1 may be freely rotated through a full 360°, and its axial position along longitudinal support 3 also may be varied. Thus, fixation screw 13 may be used to simultaneously fix longitudinal support 3 and tension bolt 28, axially and rotationally, relative to basic body 1.

Preferably, free end 23 of fixation screw 13 is configured to rest tangentially against longitudinal support 3. Free end 23 may be flat, or alternatively, it may be formed in keyed or arcuate fashion so as to positively engage tension bolt 5. Furthermore, the surfaces of free end 23 of fixation screw 13, shank 24 of tension bolt 5, and longitudinal support 3 may be textured to permit frictional engagement therebetween.

In a further preferred embodiment, clamp 100 includes a bone fixation device 11, preferably formed of a material (such as steel) which is harder than the material forming the basic body 1 (such as aluminum). By combining a comparatively hard with a comparatively soft material, for instance steel/aluminum, the design of clamp 100 may be substantially simplified. For example, such a combination is useful when affixing a bone fixation device, such as a bone screw, into clamp 100, because the bone screw is easily forced into the soft aluminum of clamp 100. A longitudinal support 3 may be affixed in an equally simple manner. The compression fixation screw 13 also may be used to force the steel body of tension bolt 5 into the softer aluminum longitudinal support 3. In general, affixation of the bone screw to the longitudinal support is improved due to these deformations as compared to mere frictional affixation. Furthermore, prior art devices implement geometric locking by serrating the various tightening elements; such devices thus require considerably higher manufacturing costs which may be avoided with the present invention. The combination of steel/aluminum additionally permits repeated use of the clamps; with the threaded tension bolt 5 being made of steel, the danger of thread overloading or freezing when positioning tension bolt 5 is minimal.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. For example, in an alternate embodiment, tension bolt 5 may be provided with two or more transverse boreholes that may be of the same or different sizes. In one alternate embodiment, one transverse borehole 10 is formed toward head 6 while another is formed toward end 7. The transverse boreholes 10 may be located on tension bolt 5 such that when a bone fixation device 11 in placed in each transverse borehole 10, one bone fixation device 11 rests on each side face 16, 17. Thus, nut 9 may not be needed for fixing bone fixation devices 11 to basic body 1. In another alternate embodiment, transverse boreholes 10 of substantially different sizes may be provided in tension bolt 5, thus accommodating a wider range of bone fixation device 11 diameters. In yet another alternate embodiment, one or more of borehole 2, borehole 4, and transverse borehole 10 may be configured and dimensioned to receive non-circular components. For example, transverse borehole 10 may have a hexagonal geometry, thus being keyed to receive bone fixation devices having similar hexagonal geometry. In other embodiments, multiple boreholes may be provided in the same basic body so that multiple longitudinal supports may be retained. Still further, a grooved region may be provided on the face of clamp 100, instead of a uniformly flat face, so that the final angulation of bone fixation device 11 may be limited to within a range of angles permitted by the groove. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A clamp for an external bone fixation device, comprising:
    a body having first, second and third boreholes extending therein;
    a longitudinal support;
    a coupling member for coupling to a bone fastener; and
    a tightening component,
    wherein the first borehole extends along a first longitudinal axis and is configured and dimensioned for receiving the longitudinal support, the second borehole extends along a second longitudinal axis and is configured and dimensioned for receiving the coupling member, and the third borehole extends along a third longitudinal axis and is configured and dimensioned for receiving the tightening component, with the first longitudinal axis being oriented at an angle with respect to the second longitudinal axis, and the third longitudinal axis being perpendicular to both the first and second longitudinal axes, and with the third borehole extending from a surface of the body to intersect the second borehole, and the first and second boreholes at least partially intersecting each other,
    wherein the longitudinal support in the first borehole and the coupling member in the second borehole are simultaneously fixed in position when the tightening component bears against the member and the member bears against the longitudinal support.

2. The clamp of claim 1, wherein the third borehole is threaded and only extends to the intersection with the second borehole, with the tightening component also being correspondingly threaded to engage the threaded borehole.

3. The clamp of claim 1, wherein the coupling member includes a first end and a second end, and a through hole proximate the first end for receiving a bone fastener and the first and second boreholes are perpendicular to each other.

4. The clamp of claim 3, wherein the coupling member further includes a threaded portion proximate the second end.

5. The clamp of claim 4, further comprising a nut for threadably engaging the threaded portion of the coupling member.

6. The clamp of claim 3, wherein the body has a rectangular form having six faces, with each face having smooth edges.

7. The clamp of claim 3, wherein the body has a rectangular form having six faces, with each face having beveled edges.

8. The clamp of claim 3, wherein the body has a parallelepiped shape.

9. The clamp of claim 3, wherein the coupling member is generally cylindrical and has a coupling member diameter, the second bore has a second diameter, and the coupling member diameter is smaller than the second diameter to permit the coupling member to freely move within the second bore.

10. The clamp of claim 9, wherein the through hole has a hole diameter, the bone fastener has a fastener diameter, and the hole diameter is about the same as the fastener diameter.

11. The clamp of claim 1, wherein the tightening component is formed of a first material and the body is formed of a second material, the first material being harder than the second material.

12. The clamp of claim 11, wherein the first material is steel and the second material is aluminum.

13. The clamp of claim 12, wherein the longitudinal support is formed of a third material, the first material being harder that the third material.

14. A clamp for an external bone fixation device, comprising:
- a longitudinal support;
- a tightening component formed of a first material; and
- a coupling member for coupling to a bone fastener,
- a body formed of a second material, the body including a first borehole configured and dimensioned for receiving the longitudinal support, a second borehole oriented at an angle with respect to the first borehole and configured and dimensioned for receiving the coupling member, and a third hole substantially perpendicular to both the first and second boreholes and configured and dimensioned for receiving the tightening component, the third hole extending from a surface of the body to intersect the second borehole, and the first and second boreholes at least partially intersecting each other,
- wherein the first material of the tightening component is harder than the second material of the body, and when the longitudinal support is disposed in the first borehole, the coupling member is disposed in the second borehole, and the tightening component is disposed in the third hole, the longitudinal support and coupling member may be simultaneously fixed in position when the tightening component bears against the coupling member and the coupling member bears against the longitudinal support.

15. The clamp of claim 14, wherein the clamp further includes a threaded coupling member fastener and the coupling member includes a first end, a second end, a through hole proximate the first end for receiving a bone fastener, and a threaded portion proximate the second end, the threaded portion being configured for threadably receiving the threaded coupling member fastener.

16. The clamp of claim 15, wherein the body has six faces and the first borehole is substantially perpendicular to the second borehole.

17. A clamp for simultaneously fixing the positions of a longitudinal member and a bone fastener with respect to each other, the clamp consisting essentially of:
- a parallelepiped body with two unthreaded holes and one threaded hole extending therein;
- a coupling member for coupling to a bone fastener;
- a nut for coupling to the coupling member; and
- a threaded tightening component,
- wherein the threaded tightening component threadably engages the threaded hole, and when the threaded tightening component bears against the coupling member, the coupling member can bear against the longitudinal member.

* * * * *